United States Patent [19]

Tucci

[11] Patent Number: 4,479,489

[45] Date of Patent: Oct. 30, 1984

[54] MECHANICALLY SELF-SEALING CLOSURE

[75] Inventor: Charles A. Tucci, Miami, Fla.

[73] Assignee: Cordis Corporation, Miami, Fla.

[21] Appl. No.: 477,597

[22] Filed: Mar. 28, 1983

Related U.S. Application Data

[63] Continuation of Ser. No. 255,714, Apr. 20, 1981, abandoned.

[51] Int. Cl.³ .............................................. A61N 1/02
[52] U.S. Cl. ............................................... 128/419 P
[58] Field of Search ..... 128/419 P, 419 PG, 218 NV, 128/272.3, 764

[56] References Cited

U.S. PATENT DOCUMENTS

| | | | |
|---|---|---|---|
| 2,957,501 | 10/1960 | Holmes | 128/272.3 |
| 3,091,240 | 5/1963 | McConnaughey et al. | 128/218 NV |
| 3,198,195 | 8/1965 | Chardack | 128/419 P |
| 3,817,240 | 6/1974 | Ayres | 128/764 |
| 3,871,382 | 3/1975 | Mann | 128/419 P |
| 3,908,668 | 9/1975 | Bolduc | 128/419 D |
| 3,977,403 | 8/1976 | Patel | 128/274 |
| 4,012,325 | 3/1977 | Columbus | 128/764 |
| 4,072,154 | 2/1978 | Andersen et al. | 128/419 P |

Primary Examiner—William E. Kamm
Assistant Examiner—Mitchell J. Shein
Attorney, Agent, or Firm—Kenway & Jenney

[57] ABSTRACT

Disclosed is a plug or closure for sealing the electrical terminal block of a cardiac pacing device from contact with body fluids while allowing access to the terminal block when the closure is in place. The closure is made of an elastomeric material and includes an upper surface containing a first concave region and a lower surface including a second concave region. The concave surfaces are connected by a self-sealing transverse slit to insure a tight seal when the plug is seated under compression within the pacing device and also to permit access to a set screw contained in the electrical terminal block when the plug is in place. Such access permits adjustment of the set screw or electrical testing while the plug is seated.

5 Claims, 4 Drawing Figures

MECHANICALLY SELF-SEALING CLOSURE

RELATED APPLICATIONS

This application is a continuation of Ser. No. 255,714 filed Apr. 20, 1981, now abandoned.

BACKGROUND OF THE INVENTION

This invention relates to implantable cardiac pacing apparatus and more particularly to a plug or closure which seals an electrical terminal block of such a pacing apparatus so as to be impervious to bodily fluids while permitting ready access to the terminal block for securing a cardiac lead or for electrical testing.

Cardiac pacemakers are employed to stimulate heart muscle when the body's own stimulatory pathways have become damaged as by disease. The electrical signals from the pacemaker regulate the heart rhythm so that the heart pumps much as it would were it under the control of a normal body's own cardiac nerve impulses. The pacing device is usually implanted beneath the skin of the patient at a location some distance from the heart. The electrical signals generated in the pacing device are transmitted from the device to the heart through an insulated conductor. One end of the conductor is thus attached to the pacing device, and the other end is attached to the heart muscle directly.

Because implantable pacing devices run on self contained batteries, the pacers must be replaced periodically when the batteries have run down. The lead from the pacer to the heart muscle, however, is usually left in place so that it is desirable to be able to disconnect the lead from the pacer at the pacer itself. In this way, the pacer can be removed leaving the lead intact, and another pacer inserted and reconnected to the same lead. Typically, the lead is attached to the pacing device at an electrical terminal block by means such as a set screw. Thus, when it is time to change the pacer, the set screw is loosened thereby allowing the lead to be disconnected from the terminal block. The new pacer is then inserted and the lead reattached to the terminal block by the set screw. It is important for reliable pacer operation that the set screw which holds the lead in electrical contact with the terminal block be shielded from fluids within the body. Such shielding protects the set screw, the terminal block and the lead from corrosion, from electrical leakage and from the accumulation of solid body materials which could interfere with the removal of the set screw when it is time to replace the pacing device. Currently known sealing devices have proved unsatisfactory for the longer term service available with newer pacing devices by allowing seepage into the terminal block of body fluids. Another disadvantage of presently known sealing devices is that they preclude access to the set screw once they are in place. Thus, when inserting a new pacing device, the set screw must be tightened, and thereafter the seal is put into place. This procedure often results in contamination and precludes permanent installation of the seal plug at the time of pacer manufacture. Also, once a pacer is in place and connected to the cardiac lead it is often desirable to make electrical contact with the set screw for testing purposes. In the prior art seals such probing was not possible while the seal was in place.

It is therefore an object of the present invention to provide a superior seal which is mechanically self-sealing and which is substantially impervious to body fluids throughout the lifetime of the pacing device.

A further object of the invention is such a seal which, when in place, still allows access to the set screw for electrical probing or for tightening or loosening the set screw when it is time to replace the pacing device.

SUMMARY OF THE INVENTION

The invention disclosed herein is for use with an implantable cardiac pacing apparatus. This apparatus has a housing including a recess terminating at an electrical terminal block. The terminal block is adapted for receiving a lead extending from the pacing apparatus to the heart muscle. This lead is secured to the terminal block by means of a set screw located within the recess in the pacer housing. Included within the pacer housing are means for generating cardiac stimulating signals at the terminal block for transmission via the lead to the heart muscle. A mechanically self-sealing closure is provided which is adapted for sealing the set screw containing recess from the surrounding body fluids by means of the plug's compression fit. This self sealing closure comprises an elastomeric plug sized for a compression fit within the recess. This plug has an upper surface including a first concave region and a lower surface including a second concave region connected by a self-sealing transverse slit. In a preferred embodiment, the recess extending to the electrical terminal block includes a circumferentially extending ridge and the plug includes a circumferentially extending groove adapted for mating with the ridge when the plug is seated within the recess. The ridge-groove combination assures that the plug remains at the desired position within the recess. Effective circumferential sealing results from the plug's compression fit within the recess and may be augmented with a medical adhesive. The transverse slit extending between the first and second concave regions allows access to the set screw when the plug is seated within the recess. Because of the tight compression fit of the plug within the recess, the slit is normally closed under the compression forces provided by the walls and circumferential ridge of the recess and the concave regions bounding the slit insure a tight seal against the intrusion of body fluids through the slit. This slit allows a tool such as a hex key driver or an electrical probe to contact the screw for tightening it, loosening it or for checking the electrical output of the pacing device.

DESCRIPTION OF THE PREFERRED EMBODIMENT

Figure 1:
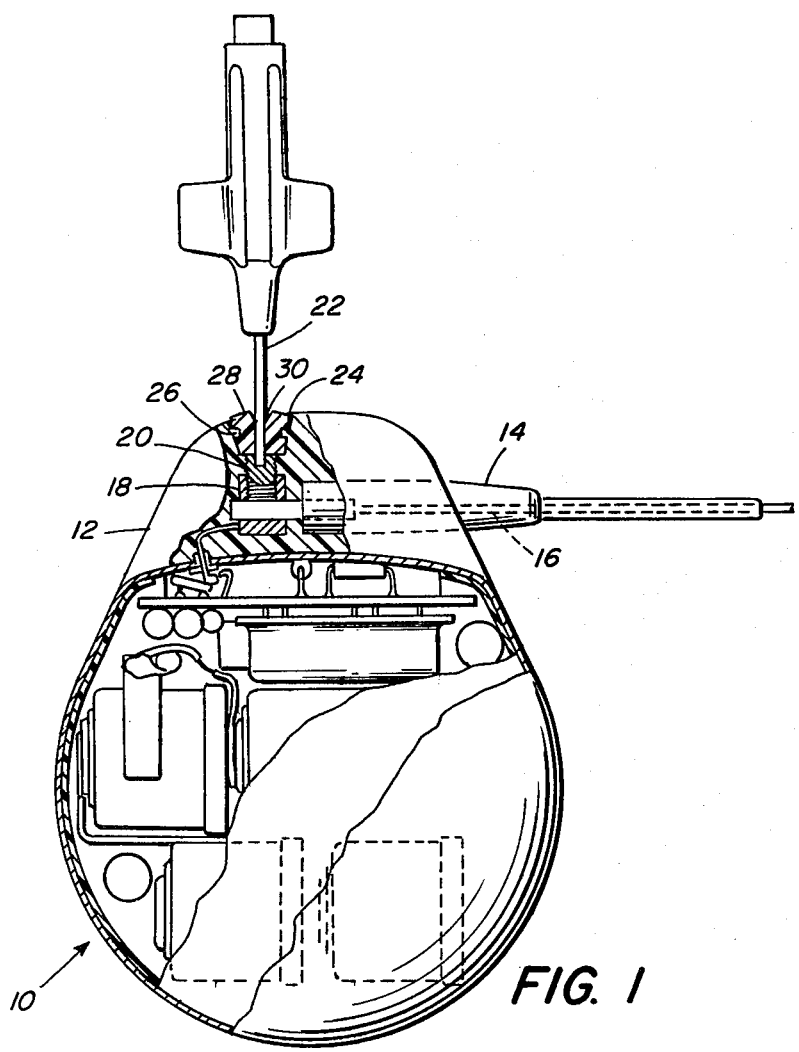
FIG. 1 is a view, partially in section, of a pacing apparatus and the closure plug disclosed herein.

With reference first to FIG. 1, a cardiac pacing apparatus 10 similar to the one disclosed in U.S. Pat. No. 4,127,134 includes a neck portion 12 which is adapted for receiving an electrical lead connector 14. Extending through the electrical connector 14 is an electrical conductor 16. The proximal tip of the electrical conductor 16 fits within a terminal block 18. The terminal block 18 is electrically connected to signal generating means within the apparatus 10. The signal generating means are conventionally known and will not be discussed further herein. The upper portion of the terminal block 18 is threaded so as to receive a set screw 20. The set screw 20 is adapted for securely holding the proximal end of the electrical conductor 16 within the terminal block 18. The set screw 20 is rotated by means of a hex key driver 22. Access to the set screw 20 is provided by a recess 24 in the neck portion 12 of the pacing apparatus 10. The recess 24 includes a circumferentially extending ridge 26. As shown in FIG. 1, the recess 24 is sealed by means of an elastomeric plug 28 which has a mating circumferential groove 29. As will be described in more detail hereinafter, the plug 28 includes a slit portion 30 which allows the hex key driver 22 to engage the set screw 20 while the plug 28 is seated within the recess 24.

Figure 2:
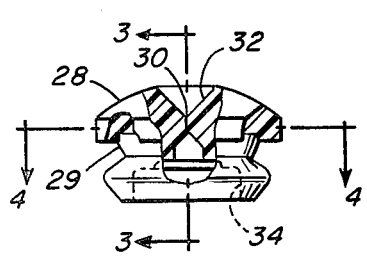
FIG. 2 is a view, partially in section, of the plug disclosed herein.
Figure 3:
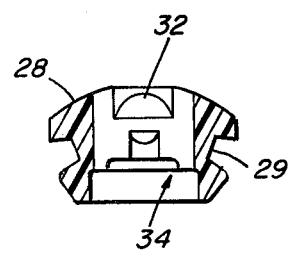
FIG. 3 is a view along section lines 3—3 of FIG. 2.
Figure 4:
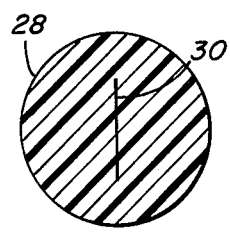
FIG. 4 is a view along section lines 4—4 of FIG. 2.

The novel closure or plug disclosed herein is shown in detail with reference to FIG. 2. The plug 28 is formed of an elastomeric material. A preferred material is medical grade elastomer manufactured by Dow-Corning under the designation Q7-4230. Other non-porous compressible materials with the property of low compression set are also suitable for the plug 28. The plug 28 has a diameter of approximately 0.22 inches and a height of 0.150 inches. The upper surface of the plug 28 has a concave region 32 and the lower surface has a lower concave region 34. The slit 30 connects the concave regions 32 and 34. The conformation of the concave regions 32 and 34 and the slit 30 are shown in more detail in the sectional views of FIGS. 3 and 4.

Referring again to FIG. 1, the plug 28 is inserted into the recess 24 in the neck portion 12 at the time the pacing apparatus 10 is manufactured. The plug 28 is secured within the recess 24 by means of a conventional adhesive material such as medical adhesive type A. The use of an adhesive material along with the mating of the ridge 26 with the groove 29 of the plug 28 insures an effective seal around the periphery of the plug 28 so that body fluids do not come into contact with the set screw 20 or the terminal block 18. Also at the time of manufacture, the surfaces bounding the slit 30 are lubricated with a silicone grease so as to facilitate the insertion of the hex key driver 22. When the driver 22 is withdrawn, the silicone grease helps assure that the slit 30 closes to form an effective seal. The radially directed compression force on the plug 28, due to its compression fit within the recess 24, causes changes in the material distribution of the plug 28. The shift in material distribution due to the radial compression coupled with the concave regions 32 and 34 concentrate the compressive forces to maintain an effective seal along the slit 30. Thus after the tool 22 is removed, the slit 30 closes, thereby effectively sealing out body fluids from the set screw 20 and electrical terminal block 18.

It is thus seen that the objects of this invention have been accomplished in that there has been disclosed a mechanically self-sealing plug for use with cardiac pacing devices. The plug is inexpensive and easy to manufacture and maintains the terminal block of a cardiac pacing apparatus free of body fluids. In addition, the plug disclosed herein permits access to the set screw for tightening or loosening or for an electrical probe for testing the electrical characteristics of the pacing device.

Variations and modifications of the invention disclosed herein will occur to those skilled in the art and it is intended that such modifications and variations fall within the scope of the appended claims.

What is claimed is:

1. In an implantable cardiac pacing apparatus comprising:
    (A) a housing including a recess terminating at an electrical terminal block;
    (B) means within said housing for generating cardiac stimulating electrical signals at said terminal block; and
    (C) an electrical lead for attachment to said terminal block by means of a set screw within said recess;
   mechanically self-sealing closure means for sealing said recess comprising an elastomeric plug consisting of:
    (1) a first concave surface;
    (2) a second opposing concave surface; and
    (3) a self-sealing transverse slit extending from said first concave surface to said second opposing concave surface, said elastomeric plug sized for a compression fit within said recess, said compression fit generating a radially directed compression force on said plug causing changes in the material distribution of said plug, whereby said changes in said material distribution coupled with said first and second concave surfaces concentrate radial compressive forces generated by said compression fit to maintain an effective seal along said transverse slit.

2. The closure of claim 1 wherein said recess has a circumferentially extending ridge and said plug has a circumferentially extending groove, said groove and said ridge adapted for mating with one another when said plug is seated within said recess.

3. The closure of claim 1 made of silastic elastomer.

4. The closure of claim 1 wherein said plug is adhesively secured within said recess.

5. In an implantable cardiac pacing apparatus comprising:
    (A) a housing including a recess terminating at an electrical terminal block, said recess including a circumferentially extending ridge;
    (B) means within said housing for generating cardiac stimulating electrical signals at said terminal block; and
    (C) an electrical lead for attachment to said terminal block by means of a set screw within said terminal block;
   mechanically self-sealing closure means for sealing said recess comprising an elastomeric plug including a circumferentially extending groove located for mating with said ridge, said plug further including
    (1) a first concave surface;
    (2) a second opposing concave surface; and
    (3) a self-sealing transverse slit extending from said first concave surface to said second opposing concave surface, said elastomeric plug sized for a compression fit within said recess, said compression fit generating a radially directed compression force on said plug causing changes in the material distribution of said plug, whereby said changes in the said material distribution coupled with said first and second concave surfaces concentrate radial compressive forces generated by said compression fit to maintain an effective seal along said transverse slit.

* * * * *